United States Patent
Zubik et al.

(10) Patent No.: US 7,789,889 B2
(45) Date of Patent: *Sep. 7, 2010

(54) APPARATUS AND METHOD FOR PRODUCING A REINFORCED SURGICAL STAPLE LINE

(75) Inventors: Joesph W. Zubik, Keller, TX (US); Chad S. McAlexander, Lafayette, IN (US); Umesh H. Patel, West Lafayette, IN (US)

(73) Assignee: Cook Biotech Incorporated, West Lafayette, IN (US)

( * ) Notice: Subject to any disclaimer, the term of this patent is extended or adjusted under 35 U.S.C. 154(b) by 156 days.

This patent is subject to a terminal disclaimer.

(21) Appl. No.: 12/021,014

(22) Filed: Jan. 28, 2008

(65) Prior Publication Data

US 2008/0125812 A1    May 29, 2008

Related U.S. Application Data (63) Continuation of application No. 10/414,432, filed on Apr. 15, 2003, now Pat. No. 7,377,928.

(60) Provisional application No. 60/372,532, filed on Apr. 15, 2002.

(51) Int. Cl.
*A61B 17/08* (2006.01)
(52) U.S. Cl. ...................................... 606/151
(58) Field of Classification Search ............... 606/148, 606/151, 219, 220, 213, 215; 227/175.1–181.1
See application file for complete search history.

(56) References Cited

U.S. PATENT DOCUMENTS

| | | | |
|---|---|---|---|
| 4,402,445 A | 9/1983 | Green | |
| 4,655,221 A | 4/1987 | Devereux | |
| 5,177,065 A | 1/1993 | Silvetti, Sr. et al. | |
| 5,263,629 A | 11/1993 | Trumbull et al. | |
| 5,356,149 A | 10/1994 | Kane | |
| 5,388,588 A | 2/1995 | Nabai et al. | |
| 5,397,324 A | 3/1995 | Carroll et al. | |
| 5,441,193 A | 8/1995 | Gravener | |
| 5,503,638 A | 4/1996 | Cooper et al. | |
| 5,527,324 A | 6/1996 | Krantz et al. | |
| 5,542,594 A | 8/1996 | McKean et al. | |
| 5,549,628 A | 8/1996 | Cooper et al. | |
| 5,575,803 A | 11/1996 | Cooper et al. | |
| 5,618,551 A | 4/1997 | Tardy et al. | |

(Continued)

FOREIGN PATENT DOCUMENTS

DE    19924311 A1    11/2000

OTHER PUBLICATIONS

International Search Report for PCT Application No. PCT/US03/11643 dated Aug. 21, 2003.

*Primary Examiner*—Anhtuan T Nguyen
*Assistant Examiner*—Tuan V Nguyen
(74) *Attorney, Agent, or Firm*—Woodard, Emhardt, Moriarty, McNett & Henry LLP (57) ABSTRACT

An apparatus for use with a surgical stapler to provide a reinforced surgical staple line. The apparatus includes an applicator that carries a first and second bioimplantable material connected by a hinge. An applicator clip may be provided to releasably secure the first and second bioimplantable material onto the applicator.

18 Claims, 3 Drawing Sheets

U.S. PATENT DOCUMENTS

| | | | |
|---|---|---|---|
| 5,690,675 A | 11/1997 | Sawyer et al. | |
| 5,702,409 A | 12/1997 | Rayburn et al. | |
| 5,752,965 A | 5/1998 | Francis et al. | |
| 5,766,188 A | 6/1998 | Igaki | |
| 5,769,892 A | 6/1998 | Kingwell | |
| 5,810,855 A | 9/1998 | Rayburn et al. | |
| 5,814,057 A | 9/1998 | Oi et al. | |
| 5,833,695 A | 11/1998 | Yoon | |
| 5,843,096 A | 12/1998 | Igaki et al. | |
| 5,902,312 A | 5/1999 | Frater et al. | |
| 5,908,427 A | 6/1999 | McKean et al. | |
| 5,948,427 A | 9/1999 | Yamamoto et al. | |
| 5,964,774 A | 10/1999 | McKean et al. | |
| 6,045,560 A | 4/2000 | McKean et al. | |
| 6,063,097 A | 5/2000 | Oi et al. | |
| 6,099,551 A | 8/2000 | Gabbay | |
| 6,273,897 B1 | 8/2001 | Dalessandro et al. | |
| 6,325,810 B1 | 12/2001 | Hamilton et al. | |
| 6,503,257 B2 | 1/2003 | Grant et al. | |
| 6,638,285 B2 | 10/2003 | Gabbay | |
| 6,730,299 B1 | 5/2004 | Tayot et al. | |
| 6,874,669 B2 | 4/2005 | Adams et al. | |
| 6,939,328 B2 | 9/2005 | Raulerson | |
| 6,939,358 B2 | 9/2005 | Palacios et al. | |
| 7,377,928 B2 * | 5/2008 | Zubik et al. | 606/151 |
| 2002/0010482 A1 | 1/2002 | Watt | |
| 2004/0093029 A1 | 5/2004 | Zubik et al. | |
| 2004/0175408 A1 | 9/2004 | Chun et al. | |
| 2005/0192628 A1 | 9/2005 | Viola | |

* cited by examiner

APPARATUS AND METHOD FOR PRODUCING A REINFORCED SURGICAL STAPLE LINE

RELATED APPLICATIONS

The present application is a continuation patent application of U.S. patent Utility patent application Ser. No. 10/414,432, filed Apr. 15, 2003, now U.S. Pat. No. 7,377,928, which claims benefit of U.S. Provisional Application Ser. No. 60/372,532, filed Apr. 15, 2002, both entitled "Apparatus And Method For Producing A Reinforced Surgical Staple Line" and both of which are incorporated by reference herein in their entirety.

TECHNICAL FIELD

The present invention relates to an apparatus for use with a surgical stapler to provide a reinforced surgical staple line. The present invention also relates to a kit for use with a surgical staple device as well as to a method of retrofitting a surgical stapler to provide reinforced surgical fastener lines.

BACKGROUND OF THE INVENTION

One of the more commercially successful innovations in surgical procedures in recent years is the development of surgical stapler devices. These devices are designed to simultaneously cut and seal an extended segment of tissue in a patient, vastly reducing the time and risks of such procedures. Typically, a surgical stapler comprises two stapler arms, one containing one or more lines of multiple staples and a second containing a corresponding structure to bend each of the staples into a closed position. For many applications, a surgical blade is included in the device to quickly sever tissue between the lines of staples. Those stapler devices employing a cutting blade are referred to as "anastomotic staplers" and those used without a cutting blade are referred to as "non-anastomotic staplers."

In the operation of a typical anastomotic stapler, the two stapler arms are positioned around tissue to be cut and then locked firmly together. In one motion, the user actuates the stapler device, which simultaneously installs two or more lines of staples through the tissue and cuts a line down the middle of the staple lines. In this manner, the user can quickly cut and seal tissue at the same time. This procedure is much faster than using a conventional process of cutting with scissors or a scalpel and then laboriously sealing the incision with sutures. As a result, patient care is dramatically improved by minimizing bleed time from the surgical site and significantly increasing the speed with which an operation can be completed.

For some procedures, the use of bare staples, with the staples in direct contact with the patient's tissue, is generally acceptable. The integrity of the tissue itself will normally prevent the staples from tearing out of the tissue and compromising the seam before healing has occurred. In certain circumstances, however, the tissue that is being sealed is too fragile to securely hold the staples in place. In these instances, the tissue will tend to rip at or near the staple lines, slowing healing and possibly leading to serious complications.

One area where fragile tissue is of particular concern is the use of stapler devices in lung tissue, and especially lung tissue that is affected by emphysema or similar condition. Diseased lung tissue is very fragile and, in extreme cases, will readily tear through unprotected staple lines. With the growing use of surgical staplers in operations on diseased lung tissues such as bullectomies and volume reduction procedures, it has become increasingly important to develop some reliable means to protect fragile tissue from tissue tears due to surgical staples or surgical stapling procedures. Moreover, when staples are used, it is desirable to reduce any leakage around the staples.

It is known to use bovine pericardial tissue as a staple line reinforcement sleeve. During an operation, a surgeon staples and cuts through both the bovine pericardial tissue and the patient's lung tissue in order to perform the lung resection procedure. Once the staples are in place, the surgeon must then cut the suture lines holding the bovine pericardial strips in place and remove the polyethylene backing material and sutures.

Other staplers such as endoscopic staplers present other difficulties. An endoscopic stapler is constructed to allow the stapler to be inserted through a small incision and then operated remotely within a patient's body by the surgeon. To accomplish this, most endoscopic staplers comprise shorter stapler arms (or "jaws") that are connected together on a fixed pivot point in a scissors fashion. The stapler arms are generally mounted remote from the surgeon's actuation means through an extended staff.

This construction presents a number of unique problems. First, it has been found that the scissors-like construction of the stapler arms tends to entrap tissue within the pivot point. This can cause fouling problems within the pivot point. Additionally, the remote nature of the endoscopic stapler can make removal of excess reinforcement material difficult from the surgical site. Finally, secure retention of reinforcement material on remote arms is a major concern for a surgeon.

In light of these problems, it is one purpose of the present invention to provide an improved staple line reinforcement material for use on a stapler that will fully protect surgical staple lines while being easy to prepare and use. It is another purpose of the present invention to provide an improved staple line reinforcement material that addresses problems unique to endoscopic staplers. These and other purposes of the present invention will become evident from review of the following specification.

SUMMARY OF THE INVENTION

The present invention provides a device for reinforcing surgical staples for surgical staplers. Surgical staplers are known and generally include a jaw that can pivot from an open to a closed position. The jaw has a first working surface and a second working surface that is opposed to the first working surface. When the jaw is closed the first and second working surfaces are in close relation to each other.

The device of the present invention includes an applicator strip that has a first end, a second end, a first face, and a second face. A first bioimplantable material has a first face that is adapted to be removably secured to a first working surface of a jaw of a surgical stapler and a second face that is juxtaposed on the first face of the applicator. A second bioimplantable material has a first face that is adapted to be removably secured to a second working surface of a jaw of a surgical stapler and a second face that is juxtaposed on the second face of the applicator. A hinge is provided to connect the first bioimplantable material to the second bioimplantable material.

Preferably, the first bioimplantable material, the second bioimplantable material, and the hinge are made of the same material. More preferably, the first bioimplantable material, the second bioimplantable material, and the hinge are formed from a single length of material. In this case, the bioimplantable material includes a first end, a second end, and a hinge located between the first and the second end. In addition, in this more preferred embodiment, the hinged portion is adjacent one end of the applicator strip such that the first and second end of the bioimplantable material are adjacent the end of the applicator strip opposite the end where the hinge is located. In this more preferred embodiment, the device may include an applicator clip that removably engages the first and second ends of the biocompatible material to hold them in contact with the corresponding end of the applicator strip.

In another embodiment of the present invention, a kit for applying a biocompatible material to the working surface of a jaw of a surgical fastener to produce a reinforced surgical fastener line includes an applicator strip having a first face and a second face, a first bioimplantable material having a first face adapted to attach to a first jaw of a surgical stapler and a second face in juxtaposed relation with the first face of the applicator strip, a second bioimplantable material having a first face adapted to attach to a second jaw of a surgical stapler and a second face in juxtaposed relation with the second face of the applicator strip, a hinge connecting the first bioimplantable material to the second bioimplantable material, and a biocompatible adhesive that removably secures the first and second biocompatible material to the working surface of the jaw. In one embodiment, the kit includes a plastic container that is sterilized and hermetically sealed.

The present invention also contemplates a method of retrofitting a surgical fastener that has a jaw with opposed working surfaces to provide reinforced surgical fastener lines. The method includes providing an applicator strip that has a first face and a second face, and a bioimplantable material having a first face and a second face with the first face in contact with the first and second face of the applicator strip, providing a bioimplantable adhesive to the second face of the bioimplantable material, and releasably attaching the biocompatible material to the working surfaces of the jaw.

Accordingly, the present invention is capable of equipping any of the known surgical fastener devices to produce reinforced suture lines by releasably attaching the first and second bioimplantable material onto an applicator such that the first and second bioimplantable materials will be manually lined up with the working surfaces of the jaw of a surgical fastener device. Advantageously, the device of the present invention is easier to prepare and use on an endoscopic surgical stapler than previous staple reinforcement devices. In addition, the ease of preparing the stapler with the device allows the stapler to function more effectively than has previously been possible. Finally, the device of the present invention is easier to manufacture than other known similar devices and therefore it represents an economical solution to the problems identified above.

In light of the foregoing, the present invention solves the various drawbacks found in the prior art. To be more specific, the present invention provides a device and method for producing reinforced surgical fastener suture lines that may be used with any type of surgical fastener, regardless of the type of surgical fastener and/or the particular shape of the surgical fastener. The device of the present invention therefore eliminates the need to create custom made surgical fasteners and/or custom made surgical fasteners in order to form reinforced suture lines.

The present invention also accomplishes the formation of reinforced surgical fastener suture lines without increasing the number of surgical fasteners within a given area, thereby minimizing the burdens associated with aligning the surgical fasteners in the cartridge with the fastener-closing depressions and/or interlocking retaining elements in the anvil. The present invention also does not require custom made disposable anvil and cartridges, thereby reducing the costs associated with providing an improved and fortified surgical fastener suture line. Finally, the device of the present invention is capable of maintaining the bioimplantable material in position next to the cartridge and/or anvil without the use of stitching or the use of a buttress member that must be removed from the surgical site following the application of the fasteners. Thus, the present invention offers wide versatility with a number of different surgical fasteners to produce reinforced surgical fastener suture lines. The fortification of surgical fastener suture lines can serve many beneficial purposes, such as providing improved vascular hemostasis, and, in the case of a pneumectomy, overcoming the natural distension of the body tissue around the surgical fasteners to achieve total air occlusion.

DESCRIPTION OF THE INVENTION

The present invention is an improved device for use in reinforcing staple lines created by a surgical stapler. In general, a conventional surgical stapler has a jaw that has two separate arms that can be locked together so that the working surface of each arm is in close contact. One arm of the jaw is loaded with one or more rows of surgical staples. The other arm is configured to bend each of the staples contained in the one arm into a closed position.

In one particular operation, the two arms of the jaw are locked together with each arm positioned on either side of the tissue to be sealed. Once the surgeon assures that the jaw is properly positioned, the staples are fired to seal the surgical site. In an anastomotic stapler device, the staples are fired simultaneously with the slicing of the tissue by a cutting blade. The result is a rapid and accurate cutting and sealing of a patient's tissue that is much faster than previous cutting and suturing techniques.

As has been noted, while commercially available staplers function well for many cutting and sealing applications, problems have been experienced with the placement of staples in relatively weak and fragile tissue, such as the lung tissue of emphysema patients. The need for some form of staple reinforcement has been recognized, but until the present invention no fully adequate staple reinforcement device has been available. The present invention, however, overcomes many of the problems previously experienced with such devices.

Figures 1A, 1B:
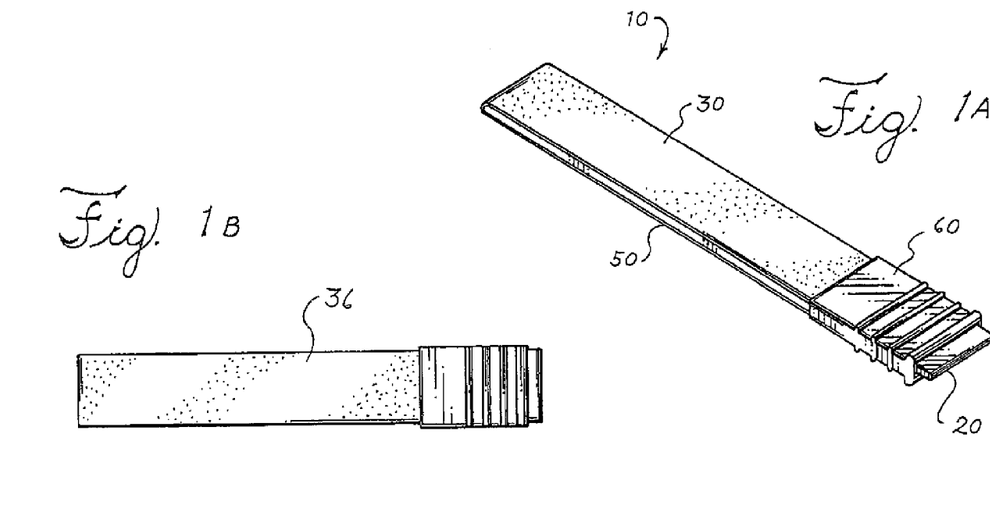
FIG. 1A is a perspective view of the device according to the present invention.
FIG. 1B is a top view of the device shown in FIG. 1A.
Figure 1C:
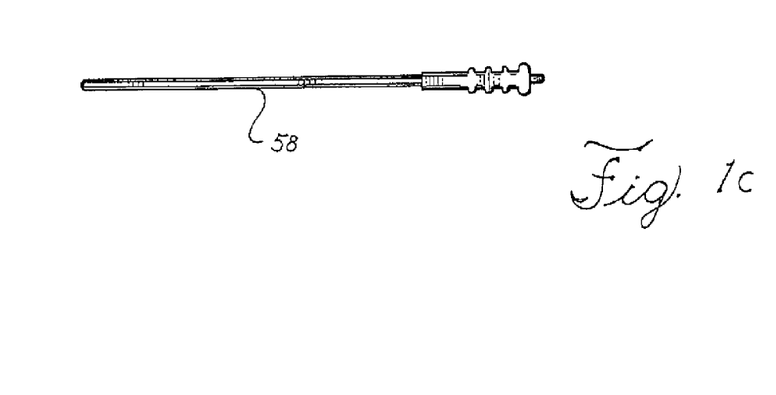
FIG. 1C is a side view of the device shown in FIG. 1A.

One embodiment of the staple reinforcement device 10 of the present invention is shown in FIGS. 1A-1C. Referring now to FIG. 1A, a perspective view of the device 10 for producing reinforced surgical fastener suture lines in accordance with a first embodiment of the present invention is shown. More specifically, the apparatus 10 of the present invention includes an applicator 20, a first bioimplantable material 30, a second bioimplantable material 50, and desirably an applicator clip 60.

Figures 2A, 2B:
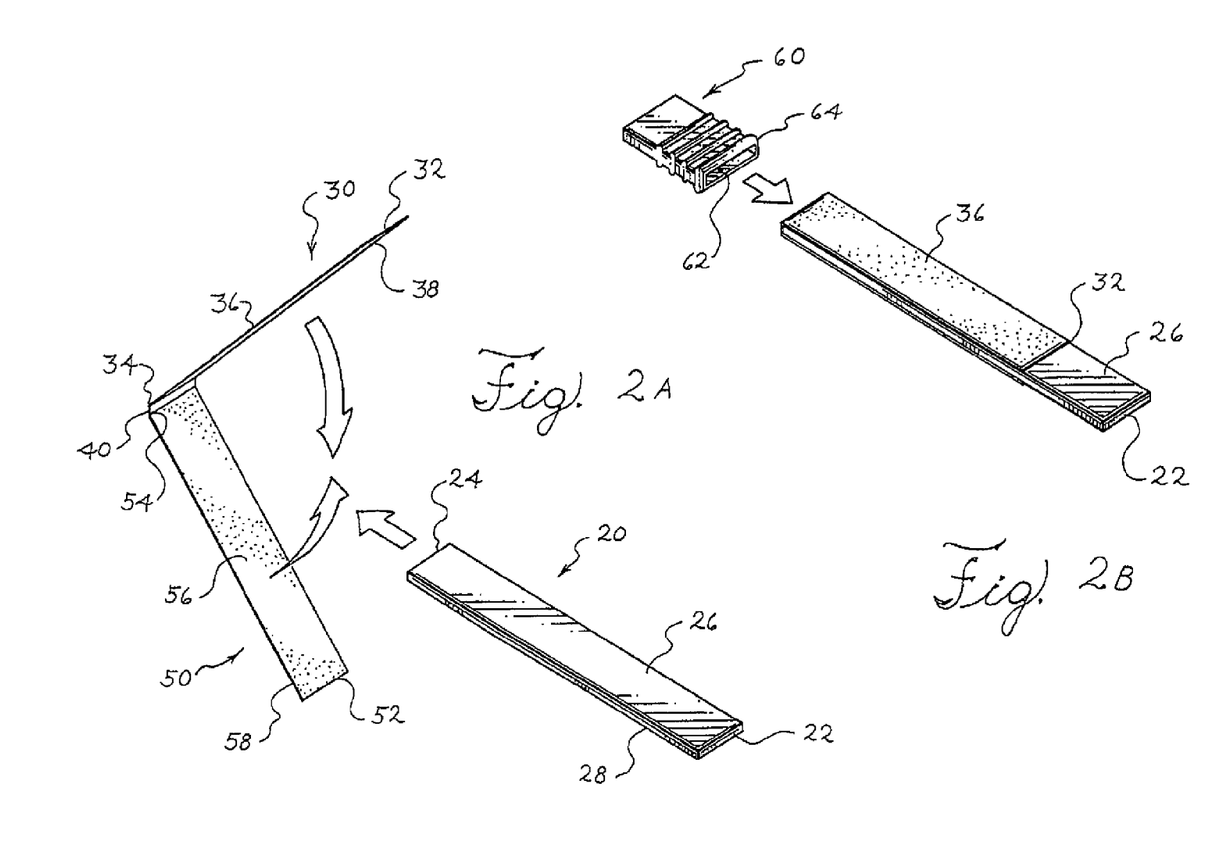
FIG. 2A shows a step in the construction of the device according to the present invention.
FIG. 2B shows another step in the construction of the device according to the present invention.

The applicator 20 has a first end 22, a second end 24, a first face 26, and a second face 28 (see FIG. 2A). The applicator is generally formed in a shape to conform to the working surfaces of the arms of the jaw of a surgical stapler. In most instances, the shape will be rectangular. It will be understood by those of skill in the art that the shape of the applicator strip will not affect the use or performance of the device 10. The applicator is formed having substantially the same dimensions as the arms of the stapler such that the assembled device can be placed between the open arms, and when the arms of the jaw of the stapler are closed, at least a portion (preferably a portion of the first end) of the applicator is exposed. Accordingly, the applicator has a shape suitable to hold the bioimplantable material, as will be discussed below, while providing the user with a convenient and easy way of positioning and aligning the device between the jaw of the stapler.

The applicator may be formed of any suitable material such as foam or the like, so long as the applicator can be provided in a sterile manner. The applicator is preferably constructed from a deformable yet resilient substrate, such as foam plastic, rubber, and/or any number of suitable materials having similar properties. The deformable and resilient nature of the applicator is desirable because it provides for a more even distribution of pressure between the working surfaces of the jaw of a surgical fastener and the first and second bioimplantable materials, respectively, when the jaw of the surgical fastener is closed to force the working surfaces into contact with the first and second bioimplantable material. By providing a uniform distribution of pressure, the applicator ensures that the first and second bioimplantable materials will more readily conform to the shape and contour of the working surfaces during the step of closing the jaw of the surgical fastener.

The first bioimplantable material 30 has a first end 32, a second end 34, a first face 36, and a second face 38 (see FIG. 2A). When the device 10 is assembled, the first end 32 is located adjacent the first end 22 of the applicator while the second end 34 is located adjacent the second end 24 of the applicator. In addition, the second face 38 is in juxtaposed relation with the first face 26 of the applicator. Typically, when the device is assembled, the second face 38 contacts the first face 26 of the applicator.

Similarly, the second bioimplantable material 50 has a first end 52, a second end 54, a first face 56, and a second face 58 (see FIG. 2A). When the device 10 is assembled, the first end 52 is located adjacent the first end 52 of the applicator while the second end 54 is located adjacent the second end 54 of the applicator. In addition, the second face 58 is in juxtaposed relation with the second face 28 of the applicator. Typically, when the device is assembled, the second face 58 contacts the first face 28 of the applicator.

A hinge 40 is provided to connect the first bioimplantable material 30 with the second bioimplantable material 50. Preferably, the hinge connects the second end 34 of the first bioimplantable material with the second end 54 of the second bioimplantable material. When the device is assembled, the hinge is located adjacent the second end 24 of the applicator. By providing a hinge in this location, when the device 10 is inserted into the open jaw of the stapler, there will not be any extending ends of the bioimplantable material that would complicate positioning of the bioimplantable material on the working surfaces of the jaw.

In a preferred embodiment of the present invention, the first bioimplantable material is the same as the second bioimplantable material. In addition, it is desirable that the hinge be formed from the same material as the first bioimplantable material and the second bioimplantable material. In a more preferred embodiment, the first bioimplantable material, the second bioimplantable material, and the hinge are formed from a single length of material.

The bioimplantable material may be selected from any known or contemplated material that may be implanted into a mammalian body. Suitable bioimplantable material includes, but is not limited to, extracellular matrices, suitable pericardium or dura matter from equine, porcine, bovine, ovine, and human, as well as bio-compatible synthetic bioimplantable materials. It is also contemplated that materials such as cat gut (collagen derived from sheep intestinal submucosa), polyglycolic acid, polylactic acid, copolymer blends of polyglycolic and polylactic acid, reconstituted collagen, polyesters, polyamino acids such as casein, albumin and the like, polyhydric alcohol polymers such as polyvinyl alcohol, cellulose glycolic acid ethers and esters of alpha-cyanoacrylic acid such as methyl alpha-cyanoacrylate may be useful.

Naturally occurring biomaterial, such as collagen, is highly desirable. In particular, a specially derived collagen material known as an extracellular matrix (ECM), such as small intestinal submucosa (SIS) is preferred. Besides SIS, examples of ECM's include pericardium, stomach submucosa, liver basement membrane, urinary bladder submucosa, tissue mucosa, and dura matter. SIS is particularly useful, and can be made in the fashion described in U.S. Pat. No. 4,902,508; U.S. Pat. No. 5,733,337; 17 Nature Biotechnology 1083 (Nov. 1999); PCT published application WO 98/22158. Irrespective of the origin of the ECM material (synthetic versus naturally occurring), the ECM material can be made thicker by making multilaminate constructs, for example SIS constructs as described in U.S. Pat. Nos. 5,968,096; 5,955,110; 5,885,619; and 5,711,969.

In addition to xenogenic biomaterials, such as SIS, autologous tissue can be harvested as well, for use as the bioimplantable material. Additionally Elastin or Elastin Like Polypeptides (ELPs) and the like offer potential as a material with exceptional biocompatibility.

In a preferred embodiment, the bioimplantable material is an ECM marketed as SIS™ from Cook Biotech Inc. This material may be provided as a single ply, two-ply, four-ply or any suitable ply as desired. Of course, the thickness of the resulting material will depend on the number of plies (layers) used. A four-ply SIS material is desirable. The thickness of the SIS™ material can be adjusted to address the needs of the intended use by adjusting the number of plies (layers). The material should not be too thick because it will then inhibit staple penetration. On the other hand, if the material is too thin, an effective seal may not be obtained. When an SIS™ material is used, a desired thickness is between about 0.30 and 0.40 mm.

As noted above, the device of the present invention preferably includes an applicator clip 60. The applicator clip is dimensioned to surround the first and second bioimplantable materials that have been placed on the applicator. When the device is assembled, the applicator clip holds the first end 32 and the second end 52 of the respective first and second bioimplantable materials in substantial contact with the applicator. As a result, the first and second bioimplantable materials are more easily transferred to the working surfaces of the jaw of the surgical fastener. In addition, the clip is dimensioned such that it can be easily removed from the applicator before the bioimplantable material is transferred to the working surfaces of the jaw of the stapler. In particular, the applicator clip is dimensioned such that it has at least a single wall to define an aperture 62 in which the applicator can be slidably received.

Referring now to FIGS. 2A and 2B, the assembly of the device according to the present invention is shown. Assembly of the device will now be described. A first and second bioimplantable material connected by a hinge having dimensions suitable for mating with the arms of a surgical stapler is provided. An applicator strip having substantially the same dimensions as the first and second bioimplantable material is provided. With specific reference to FIG. 2A, the applicator strip, the first and the second bioimplantable materials are each rectangular in shape. The hinge portion is located adjacent the second end of the applicator strip while the first ends of the first and second bioimplantable material are located adjacent the first end of the applicator. With specific reference to FIG. 2B, the first and second bioimplantable material and the hinge are provided as a single piece of material so that the material is folded over the applicator.

To secure the bioimplantable material onto the applicator, the applicator clip is slidably attached onto the applicator by moving it in a direction from the second end of the applicator toward the first end. When assembled, the first end of the applicator clip is adjacent the first end of the applicator. Advantageously, the free ends of the first and second bioimplantable materials are held in place until the applicator clip is removed. The device of the present invention is now ready for use with a surgical stapler.

The device of the present invention produces reinforced surgical fastener suture lines by equipping the jaw of a surgical fastener applying device with a first bioimplantable material and a second bioimplantable material such that, when clamped about a portion of body tissue and fired, the surgical fastener applying device will fixedly attach the first and second articles of bioimplantable material between a plurality of surgical fasteners and the subject body tissue. Positioning the first and second bioimplantable materials in this fashion effectively minimizes the degree to which fluid leakage and/or tissue tearing occurs along the suture line. The propensity for fluid leakage is reduced in that the first and second bioimplantable materials provide a more uniform distribution of pressure along the surgical fastener suture line, thereby increasing the contact area between the compressed portions of body tissue. The propensity for tissue tearing is also reduced because the first and second bioimplantable materials provide added structural support between the subject body tissue and the surgical fasteners, thereby reducing the tendency of the individual surgical fasteners to tear through diseased and/or weakened body tissue.

The device of the present invention is designed for use with any number of surgical fastener devices, including but not limited to those having pivotally related jaw members, such as those disclosed in U.S. Pat. No. 4,354,628 to Green and U.S. Pat. No. 5,141,144 to Foslien et al., and those having linearly translatable jaw members, such as those disclosed in U.S. Pat. No. 4,568,009 to Green and U.S. Pat. No. 4,508,253 to Green.

Referring collectively to FIGS. 3A through 3D, the method of retrofitting a surgical stapler is schematically shown. A portion of the stapler having a jaw 70 with a first arm 80 and a second arm 90 is shown. The first and second arms each have a working surface 82 and 92, respectively.

Figures 3A, 3B, 3C, 3D:
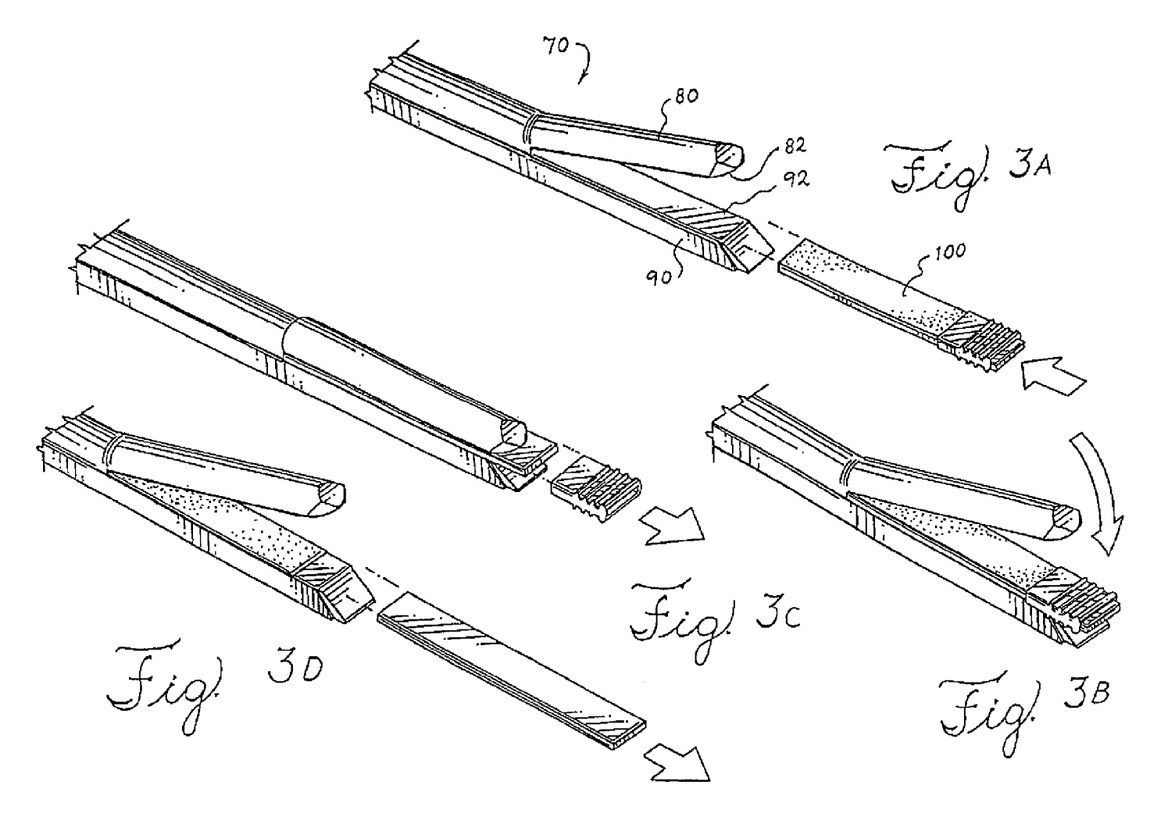
FIG. 3A shows a step in the use of the device of the present invention where the device is being inserted into the jaw of a stapler after the adhesive has been applied.
FIG. 3B shows another step in the use of the device of the present bioimplantable invention where the jaw of the stapler is being closed to join the strip of bioimplantable material to the working surface of the arms of the jaw of the stapler.
FIG. 3C shows another step in the use of the device of the present invention where the applicator clip is removed.
FIG. 3D shows another step in the use of the device of the present invention where the jaws of the stapler are opened and the applicator strip is removed.

In order to equip a surgical fastener device (i.e., stapler) to produce reinforced surgical fastener suture lines in accordance with the present invention, a releasable bond must be formed between the first and second bioimplantable material and the working surfaces of the jaw of the surgical fastener such that the first and second bioimplantable materials may be removed from the applicator and temporarily positioned on the working surfaces of the jaw of the surgical fastener. In a preferred embodiment, and as shown in FIG. 3A, a releasable bond is provided by applying an effective amount of an adhesive 100 to the first face of the first and second bioimplantable materials.

The adhesive 100 is in general a tacky liquid substance that is biocompatible. The adhesive may include, but is not necessarily limited to, a hydrogel, hydroxypropylmethyl cellulose, propylene glycol, and similar materials. It is understood by one of skill in the art that a wide variety of different adhesives may be used, including but not limited to contact adhesives, such as polyacrylamides and natural gum rubbers applied during the manufacturing process, and hydrogels and other similar compounds which may be applied at the time of use. With specific regard to those adhesives applied during the manufacturing process, it is also contemplated to provide a protective film or covering over the adhesive layer to maintain the bioimplantable material sterile prior to use. The use of such a protective film may also reduce the amount of time required to prepare the device for use because the user would not have to spend time manually applying the adhesive to the first and second bioimplantable materials, as described above. Rather, the user could simply peel away the protective film to reveal the adhesive on the first and second bioimplantable materials.

It is also contemplated that the first and second bioimplantable materials may be temporarily attached to the working surfaces of the jaw by applying the adhesive directly to the working surfaces. In this arrangement, the surgical fastener may then be closed about the applicator to form the requisite temporary bond between the working surfaces of the jaw and the bioimplantable material such that the surgical fastener may be thereafter opened with the bioimplantable material temporarily affixed to the working surfaces of the jaw.

Alternatively, it is possible to design the jaw with pneumatic suction capability such that a suction bond forms between the bioimplantable material and the working surfaces of the jaw when the surgical fastener is closed onto the applicator. This could be accomplished by providing an air line in fluid communication with each working surface and drawing air into the plane defined by the working surface in an amount sufficient to form a bond between the working surface and the bioimplantable material.

Thereafter, the assembled device 10 is moved toward the open arms of the stapler with the second end of the applicator moving toward the pivot point of the jaw. The applicator has a length that is somewhat greater than the length of the arms. By dimensioning the applicator in this fashion, the applicator can be inserted between the open arms to the pivot point such that the second end of the applicator is adjacent the pivot point of the jaw. This aids in aligning and positioning the bioimplantable members in conjunction with the working surfaces of the arms.

As shown in FIG. 3B, the arms of the stapler are then moved to a closed position such that the first face 36 of the first bioimplantable material contacts the working surface 82 of one arm 80 and such that the first face 56 of the second bioimplantable material contacts the working surface 92 of the other arm 90. The arms are maintained in a closed position for a given period of time. The adhesive 100 forms a sufficient, yet temporary bond between the first and second bioimplantable materials and the working surfaces of the jaw surgical fastener such that, when the surgical fastener is opened from the previously clamped position, the first and second bioimplantable materials remain releasably attached to the working surfaces of the jaw of the surgical fastener.

As shown in FIG. 3C, the applicator clip is removed before opening the jaw. Then, as shown in FIG. 3D, the jaw can be opened so that the applicator can be removed. The surgical fastener is then fully equipped with the first and second bioimplantable materials so that the working surfaces may be positioned about a section of body tissue to form a reinforced surgical fastener suture line in accordance with the present invention.

The device of the present invention effectively ensures a consistent method of engagement with the particular surgical fastener so that the first and second bioimplantable materials will always be applied to the working surfaces of the jaw of the surgical fastener in the desired and proper manner. In addition, the device of the present invention allows a physician to quickly and easily retrofit a prior art surgical fastener to produce reinforced suture lines without undertaking painstaking efforts to properly position the bioimplantable material on the surgical fastener.

With reference now to FIG. 3D, the surgical fastener is ready for use. In this condition, the first and second bioimplantable materials are releasably disposed on the working surfaces of the jaw.

In a typical configuration, one arm of the jaw will be equipped with a fastener cartridge having at least one row of fasteners, while the second arm will be furnished with an anvil having fastener-closing depressions and/or interlocking retaining elements aligned with the row of fasteners. The surgical fasteners used may include, but are not necessarily limited to, conventional staples and/or two-piece interlocking fasteners constructed from metal and/or non-metallic resinous material. When using with conventional staples, the present invention ensures that the surgical fastener will drive the staple legs through the one bioimplantable material (either the first bioimplantable material or the second bioimplantable material, depending on which arm carries the fasteners), the subject body tissue, and the other bioimplantable material before being cinched by depressions formed in the other arm to secure the first and second bioimplantable materials on either side of the subject body tissue.

With regard to two-piece surgical fasteners, use of the device of the present invention will similarly ensure that the legs of the fasteners will be driven through the first bioimplantable material, the subject body tissue, and the second bioimplantable material before being interlocked with retainer members disposed within an arm of the jaw to secure the first and second bioimplantable materials about the compressed body tissue. As such, the surgical fastener may create a reinforced surgical fastener suture line by simply closing the first and second arms of the jaw upon a portion of body tissue and firing a surgical fastener applying device to drive fasteners from one arm to sandwich a portion of body tissue between the first and second bioimplantable materials.

Advantageously, the present invention contemplates a kit that includes a vacuum molded plastic container that is sterilized and hermetically sealed and contains the device of the present invention and the adhesive in a convenient and ready-to-use condition. In a preferred embodiment, the device of the present invention will be prepared at the manufacturing site. In other words, the first and second bioimplantable materials will be disposed on the applicator, and the clip, when provided, will be located on the applicator. In this arrangement, the device of the present invention can be quickly and efficiently used to prepare a surgical fastener device for producing reinforced surgical fastener suture lines.

Alternatively, the kit of the present invention may include an inner pouch formed from high density polyethylene, such as that marketed under TYVEK, which is then sealed to provide a sterile environment. The inner pouch contains the bioimplantable material, the applicator, and the clip. The inner pouch may then be placed into an outer pouch, which is preferably formed from high density polyethylene (e.g., TYVEK) and provides a sterile environment for the inner pouch. Both the inner pouch and, where provided, the outer pouch can be packaged in a carton or similar container.

The surgical stapler can be retrofitted to provide reinforced stapler lines in the following manner. The device of the present invention and the tube of adhesive are removed from the sterile package. Then, the adhesive is spread onto the first face of the first and second bioimplantable materials. The applicator is then positioned in general alignment with the working surfaces of a jaw of a surgical fastener. The arms of the jaw are closed onto the adhesive-coated first and second bioimplantable materials to compress the applicator. The applicator clip is removed so that the bioimplantable material can be transferred to the working surfaces of the arms of the jaw. The arms of the jaw are then opened with the first and second bioimplantable materials adhered to the working surfaces. The applicator is removed and then the working surfaces of the arms of the jaw are positioned over a designated portion of body tissue. The arms are closed about the subject body tissue. The fasteners are fired to form a reinforced surgical fastener suture line. The arms of the jaw are opened and the fastener is removed from the site of the suture line.

While there have been described what are presently believed to be the preferred embodiments of the invention, those skilled in the art will realize that changes and modifications may be made thereto without departing from the spirit of the invention. It is to be understood that the invention can be carried out by specifically different equipment and devices, and that various modifications, both as to the equipment details and operating procedures, can be accomplished without departing from the scope of the invention itself.

The invention claimed is:

1. A method of loading a bolster material onto a surgical stapling device, the method comprising:

providing a surgical stapling device having a receiving area for receipt of a bolster material, the receiving area including a first surface and a second surface;

providing a loading device for loading a single piece of bolster material onto the surgical stapling device, the loading device comprising:

an applicator element having a first applicator face for holding a first portion of said single piece of bolster material, and a second applicator face for holding a second portion of said single piece of bolster material;

a single piece of bolster material removably positioned on the applicator element, the single piece of bolster material including a first bolster material portion having a face received on said first applicator face, a second bolster material portion having a face received on said second applicator face, and a bend portion connecting said first bolster material portion and said second bolster material portion, wherein said first bolster material portion, said second bolster material portion, and said bend portion are formed from a single piece of bovine pericardium;

a clip element into which the applicator element and bolster material are received for holding the bolster material in contact with the applicator element, the clip element having a proximal handle portion and a distal receiving portion, the applicator element only partially received within the clip element such that a distal region of the applicator element extends distally beyond the distal receiving portion of the clip element; and an adhesive material on a surface of said single piece of bolster material for adhering said single piece of bolster material to said surgical stapling device; and delivering the loading device to the surgical stapling device such that the single piece of bolster material is received in the receiving area, and such that the face of the first bolster material portion contacts and is held against the first surface of the receiving area and the face of the second bolster material portion contacts and is held against the second surface of the receiving area.

2. The method of claim 1, further comprising contacting said surgical stapling device with said adhesive material such that said single piece of bolster material is adhered to said surgical stapling device.

3. The method of claim 1, further comprising removing said loading device from a sealed medical package in which said loading device is contained.

4. The method of claim 3, wherein said loading device is sterilely packaged in said sealed medical package.

5. The method of claim 1, further comprising removing a covering material from said loading device, said covering material removably adhered to and covering said adhesive material on said single piece of bolster material.

6. The method of claim 5, further comprising removing said loading device from a sealed medical package in which said loading device is contained.

7. The method of claim 1, wherein said adhesive material includes a hydrogel.

8. The method of claim 1, wherein said adhesive material is a tacky substance.

9. A method of loading a bolster material onto a surgical stapling device, the method comprising:

providing a surgical stapling device having a receiving area for receipt of a bolster material, the receiving area including a first surface and a second surface;

providing a loading device for loading a single piece of bolster material onto the surgical stapling device, the loading device comprising:

an applicator element having a first applicator face for holding a first portion of said single piece of bolster material, and a second applicator face for holding a second portion of said single piece of bolster material;

a single piece of bolster material removably positioned on the applicator element with a portion of the applicator element extending beyond the bolster material, the single piece of bolster material including a first bolster material portion having a face received on said first applicator face, a second bolster material portion having a face received on said second applicator face, and a bend portion connecting said first bolster material portion and said second bolster material portion, wherein said first bolster material portion, said second bolster material portion, and said bend portion are provided by a single length of an extracellular matrix material;

a clip element into which the applicator element and bolster material are received for holding the bolster material in contact with the applicator element, the clip element having a proximal handle portion and a distal receiving portion, the applicator element only partially received within the clip element such that a distal region of the applicator element extends distally beyond the distal receiving portion of the clip element; and an adhesive material on a surface of said single piece of bolster material for adhering said single piece of bolster material to said surgical stapling device; and delivering the loading device to the surgical stapling device such that the single piece of bolster material is received in the receiving area, and such that the face of the first bolster material portion contacts and is held against the first surface of the receiving area and the face of the second bolster material portion contacts and is held against the second surface of the receiving area.

10. The method of claim 9, wherein said extracellular matrix material is selected from the group consisting of pericardium, submucosa, liver basement membrane and dura mater.

11. The method of claim 10, wherein said extracellular matrix material is pericardium.

12. The method of claim 9, wherein said single length of said extracellular matrix material includes a multilaminate extracellular matrix material.

13. The method of claim 9 further comprising removing a covering material from said loading device, said covering material removably adhered to and covering said adhesive material on said single piece of bolster material.

14. A method of loading a bolster material onto a surgical stapling device, the method comprising:

providing a surgical stapling device having a receiving area for receipt of a bolster material, the receiving area including a first surface and a second surface;

providing a loading device for loading a single piece of bolster material onto the surgical stapling device, the loading device comprising:

an applicator element having a first applicator face for holding a first portion of said single piece of bolster material, and a second applicator face for holding a second portion of said single piece of bolster material;

a single piece of bolster material removably positioned on the applicator element, the single piece of bolster material including a first bolster material portion having a face received on said first applicator face, a second bolster material portion having a face received on said second applicator face, and a bend portion connecting said first bolster material portion and said second bolster material portion, wherein said first bolster material portion, said second bolster material portion, and said bend portion are provided by a single length of an extracellular matrix material;

a clip element into which the applicator element and bolster material are received for holding the bolster material in contact with the applicator element, the clip element having a proximal handle portion and a distal receiving portion, the applicator element only partially received within the clip element such that a distal region of the applicator element extends distally beyond the distal receiving portion of the clip element; and an adhesive material on a surface of said single piece of bolster material for adhering said single piece of bolster material to said surgical stapling device; and delivering the loading device to the surgical stapling device such that the single piece of bolster material is received in the receiving area with an exposed portion of the applicator element extending beyond the receiving area, and such that the face of the first bolster material portion contacts and is held against the first surface of the receiving area and the face of the second bolster material portion contacts and is held against the second surface of the receiving area.

15. The method of claim 14, wherein said extracellular matrix material is selected from the group consisting of pericardium, submucosa, liver basement membrane and dura mater.

16. The method of claim 15, wherein said extracellular matrix material is pericardium.

17. The method of claim 14, wherein said single length of said extracellular matrix material includes a multilaminate extracellular matrix material.

18. The method of claim 14 further comprising removing a covering material from said loading device, said covering material removably adhered to and covering said adhesive material on said single piece of bolster material.

* * * * *